US007132083B2

(12) United States Patent  
Martin

(10) Patent No.: US 7,132,083 B2
(45) Date of Patent: Nov. 7, 2006

(54) APPARATUS FOR REMOVING STERILANT FROM A STERILANT CONTAINING ATMOSPHERE

(75) Inventor: Anthony Martin, Andover (GB)

(73) Assignee: Bioquell UK Limited, Andover (GB)

( * ) Notice: Subject to any disclaimer, the term of this patent is extended or adjusted under 35 U.S.C. 154(b) by 405 days.

(21) Appl. No.: 10/276,193

(22) PCT Filed: Aug. 2, 2001

(86) PCT No.: PCT/GB01/03462

§ 371 (c)(1),
(2), (4) Date: Nov. 13, 2002

(87) PCT Pub. No.: WO02/11864

PCT Pub. Date: Feb. 14, 2002

(65) Prior Publication Data

US 2003/0143125 A1    Jul. 31, 2003

(30) Foreign Application Priority Data

Aug. 4, 2000  (GB) ................................ 0019214.6

(51) Int. Cl.
*A62B 11/00* (2006.01)
(52) U.S. Cl. ........................ 422/122; 422/28; 422/124; 96/108
(58) Field of Classification Search .................... 422/4, 422/28, 122, 124; 96/223, 233, 108
See application file for complete search history.

(56) References Cited

U.S. PATENT DOCUMENTS 2,146,071 A * 2/1939 Horvath ........................ 96/142
5,015,442 A * 5/1991 Hirai ............................ 422/121
5,906,794 A    5/1999 Childers
5,997,619 A * 12/1999 Knuth et al. .................. 96/224

FOREIGN PATENT DOCUMENTS

| DE | 34 05 142 A1 | 9/1985 |
| DE | 36 42 674 A1 | 6/1988 |
| DE | 199 45 500 A1 | 4/2000 |
| EP | 0 882 492 A1 | 12/1998 |
| JP | 1-269846 | 10/1989 |
| JP | 11-221443 | 8/1999 |

* cited by examiner

*Primary Examiner*—Krisanne Jastrzab
*Assistant Examiner*—Sean E. Conley
(74) *Attorney, Agent, or Firm*—Workman Nydegger

(57) ABSTRACT

An apparatus for removing a sterilant from a sterilant containing atmosphere of a room includes an enclosure having an inlet to receive sterilant containing air from the room following sterilization of the room, outlet nozzles to return air from which sterilant has been removed to atmosphere, and a catalyst within the enclosure for removing sterilant from the air. A fan draws sterilant containing air from the inlet through the catalyst and thence to atmosphere. An additional fan is provided to circulate air containing sterilant from the room during a room sterilization process through that part of the enclosure which is downstream of the catalyst to ensure sterility of that part of the enclosure for the sterilant removal phase.

7 Claims, 1 Drawing Sheet

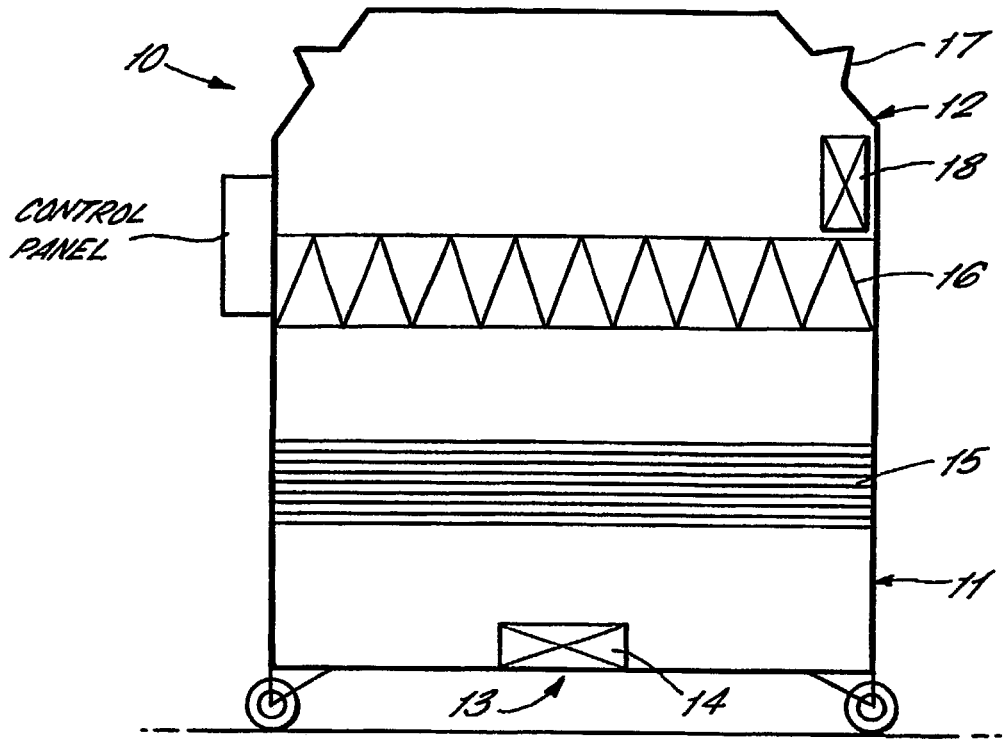
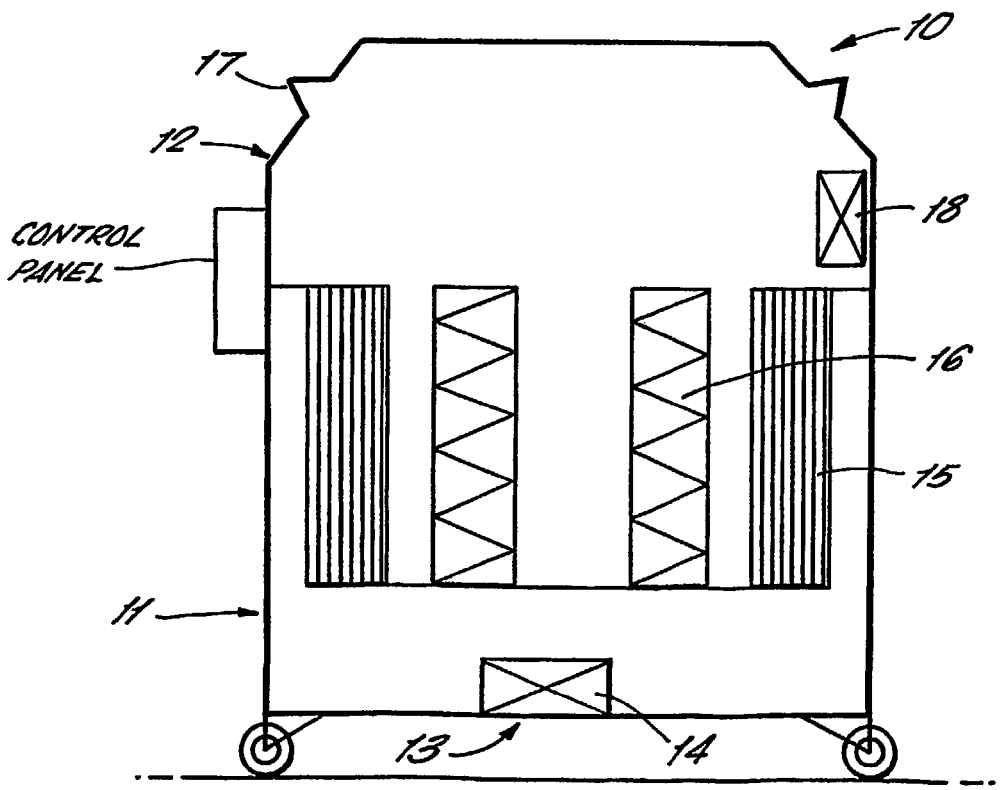

APPARATUS FOR REMOVING STERILANT FROM A STERILANT CONTAINING ATMOSPHERE

BACKGROUND OF THE INVENTION

1. Field of the Invention

This invention relates to an apparatus for removing a sterilant from a sterilant containing atmosphere in a room or other enclosure. A method of removing hydrogen peroxide gas from a room following gaseous surface sterilisation.

2. Relevant Technology and Summary of the Invention

It is frequently necessary to sterilise the surfaces inside clean rooms in which pharmaceutical manufacturing processes are operated. Similar sterilising is also required in the biotechnology, biomedical and health care industries.

The traditional technique used for the sterilisation process has been to generate formalin vapour and allow this to remain in the room for a period of time and then using an air extraction system to remove the formalin by dilution until it is safe to re-enter the room. This technique although effective in reducing the bio-burden has the disadvantage that it leaves a residue of para-formaldehyde which is persistent and causes an unpleasant smell.

More recently it has been possible to use gaseous hydrogen peroxide as the sterilising agent. This has the advantage of breaking down to water and oxygen, and therefore does not leave a residue. When properly applied it is also a much faster process than fumigation with formalin but there is still the problem of removing the residual gas once sterilisation has been achieved.

With hydrogen peroxide it is generally true that the largest phase of a sterilisation cycle will be the time for aeration to remove the residual gas to a safe level. Frequently it is possible to use the room ventilation system to extract the air and residual hydrogen peroxide gas, but in some buildings this may not be possible. If for example there is a common extract system, with some percentage of re-circulation then the extracted air containing the hydrogen peroxide may be circulated back to other areas and under such circumstances it is desirable to have an alternative aeration technique.

As a good general rule it may be assumed that by doubling the air extraction rate after hydrogen peroxide sterilisation it is possible to halve the time required to remove the active gas.

Most of the commercially available hydrogen peroxide gas generators circulate the gas through the room to be sterilised and then back to the generator. The air that is returned to the generator is then processed and further amounts of hydrogen peroxide gas are added. At the end of a gassing phase of a sterilisation cycle the air continues to circulate through the gas generator but the returning hydrogen peroxide is decomposed in the generator to water and oxygen. This circulating process breaking down the hydrogen peroxide would eventually remove all of the active gas from the room, but as this circulating flow is small the time taken to reduce the gas concentration would be very long.

JP-A-11221443 discloses a method of reducing the release of hydrogen peroxide from a sterilisation chamber in which hydrogen peroxide is used as the active sterilant. The chamber has a vacuum pump for withdrawing gases from the chamber and discharging them to atmosphere. Catalytic converters are located in the conduit between the chamber and inlet to the pump and between the outlet to the pump and the outlet to atmosphere to convert hydrogen peroxide flowing in the conduit into oxygen and hydrogen to reduce the concentration of hydrogen peroxide released at the outlet.

DE-A-199 45 500 discloses a method and apparatus as described and illustrated for sterilising containers in a filling machine, which are intended for the filling in particular of liquid or pasty foodstuffs, wherein the containers are flushed with hydrogen peroxide ($H_2O_2$) immediately before the filling operation and the filling operation is carried out in a sterile environment, wherein the $H_2O_2$ contained in the exhaust air is decomposed to $H_2O_2$ and $O_2$ in a catalyst, and wherein the resultant sterile air serves to remove the hydrogen peroxide from the containers. For optimisation in respect of efficiency, environmental compatibility and process safety there is provision for the sterile air to form a laminar flow in the interior of the filling machine and for it to be used to seal the filling chamber by the surplus air volume being released into the environment.

DE-A-36 42 674 A1 discloses the sterilisation of filling installations and packing installations used for packing foodstuff and in the pharmaceutical industries. Hydrogen peroxide is often used in such applications. The hydrogen peroxide can be broken down after use with the aid of a platinum or palladium catalyst. However such catalysts decline in effectiveness in a relative short period of use. This difficulty can be overcome by the provision of a catalyst support in which a support body consists of carbon particles bonded together without binder, the common particles comprising a first carbon fraction which forms the support skeleton and a second carbon fraction of highly porous activated carbon with an inorganic catalytically active substance, in particular noble metals and their compounds, applied to the support body and/or the activated carbon particles to break down hydrogen peroxide flowing through the body.

It is an object of this invention to provide an apparatus for removing the sterilant such as hydrogen peroxide from an atmosphere in a room containing the sterilant without causing the circulation used to remove the sterilant from the atmosphere to contaminate the room.

This invention provides an apparatus for removing a sterilant from a sterilant containing atmosphere of a room comprising an enclosure having an inlet to receive sterilant containing air from the room following sterilization of the room, an outlet to return air from which sterilant has been removed to atmosphere, a catalyst within the enclosure for removing sterilant from the air, means for drawing sterilant containing air from the inlet through the catalyst and thence to atmosphere and means to circulate air containing sterilant from the room during a room sterilization process through that part of the enclosure which is downstream of the catalyst to ensure sterility of that part of the enclosure for the sterilant removal phase.

Preferably a filter is located in the enclosure between the inlet and outlet to filter air passing therethrough.

More specifically the filter may be located downstream of the catalyst and to be sterilized by supplemental means for drawing sterilant through the enclosure downstream of the catalyst during the room sterilization process.

In any of the above arrangements the catalyst may be a carbon filter.

Also in any of the above arrangements the outlet may comprise a nozzle or nozzles for directing the stream of air from which sterilant has been removed into the atmosphere around the enclosure to create turbulence in the air.

The supplemental means to draw sterilant through the part of the enclosure downstream of the catalyst during the room sterilization process may comprise further fan means of relatively low throughput compared with the first mentioned fan means, the further fan means having a further inlet disposed in said enclosure on said downstream side of the catalyst to draw air containing steriliant from the atmosphere into the enclosure during the room sterilization process and to circulate air through the downstream side of the enclosure to sterilize that part of the enclosure, the air containing steriliant being released from the enclosure by said outlet from the enclosure.

The apparatus may be mounted on, wheels to be readily mobile.

The present invention provides a rapid method of removing the active gas from the room without the necessity of providing an additional extract system.

BRIEF DESCRIPTION OF THE DRAWINGS

The following is a description of some specific embodiments of the invention, reference being made to the accompanying drawings in which:

FIGS. 1 and 2 are diagrammatic views of mobile apparatus for removing steriliant from the air.

DETAILED DESCRIPTION OF THE PREFERRED EMBODIMENTS

The apparatus consists of a mobile container 10 having a lower casing 11 and a removable top cover 12. The lower case has an air inlet 13 in the bottom wall of the casing, a high capacity fan mounted in the casing directly above the inlet and a carbon catalyst 15 extending across the full width and length of the casing above the fan. An HEPA filter 16 extends across the casing above the catalyst.

The fan 14 draws air from the room and drives it through the catalyst or activated carbon filter 15. A suitable catalyst would be Ruthenium and the activated carbon is a special grade, which will decompose hydrogen peroxide. Any hydrogen peroxide gas passing through the catalyst or carbon filter will be decomposed to water and oxygen. On leaving the catalyst or carbon filter 15 the air passes through a HEPA Filter 16 to remove any particulate matter ensuring that the air being returned to the clean room matches the specification required within the room.

The air leaves the apparatus through one of a series of adjustable nozzles, 17 placed around the top cover 12.

The nozzles produce jets of high speed air to ensure good mixing of the air within the room ensuring that there are no pockets of residual gas.

On the side of the apparatus is a control panel which may be detached and placed remotely so that the equipment may be operated from outside of the area to be sterilised either manually or by a connection to the gas generator which will activate the device when it is required to aerate the room.

During the sterilising phase of the room a small fan 18 positioned in the casing lid 12 operates drawing the room air containing sterilisation gas into the top cover through an inlet (not shown). This ensures that the surfaces downstream of the filter 16 inside the device are sterile and hence will not cause contamination to the room after sterilisation.

The problem with any aeration system placed within a room is to ensure that it cannot cause contamination of the room in which it is placed. Within the aeration unit the space above the HEPA (Particulate Air Filter) 16 will be non-sterile, because it will have been exposed to non-sterile air.

This problem is overcome as indicated above by drawing some of the sterilising gas, during the gassing process, into this space and hence causing decontamination. If this space is not decontaminated then, when the aeration unit is used to remove the sterilising gas from the room, there is a danger of passing any contamination from this enclosed space in the aeration unit out into the decontaminated room.

An alternative arrangement of the apparatus is shown in FIG. 2, which functions in precisely the same way. The difference in the embodiment of FIG. 2 is that both the catalyst and carbon filter 15 and the HEPA Filter 16 are circular and not of rectangular construction. The circular construction has the advantage that a larger filter face area is possible in the same size footprint.

The invention claimed is:

1. An apparatus for removing a steriliant from a steriliant containing atmosphere of a room, the apparatus comprising:
    an enclosure having an inlet to receive steriliant containing air from the room following sterilization of the room;
    an outlet to return air from which steriliant has been removed to atmosphere;
    a catalyst within the enclosure for removing steriliant from the air;
    means for drawing steriliant containing air from the inlet through the catalyst and thence to the atmosphere; and
    means for circulating air containing steriliant from the room during a room sterilization process through that part of the enclosure which is downstream of the catalyst to ensure sterility of that part of the enclosure for the steriliant removal phase, the means for circulating being separate from the means for drawing.

2. An apparatus as claimed in claim 1, further comprising a filter located in the enclosure between the inlet and the outlet to filter air passing threrethrough.

3. An apparatus as claimed in claim 2, wherein the filter is located downstream of the catalyst and is sterilized by the means for circulating air containing steriliant through the enclosure downstream of the catalyst during the room sterilization process.

4. An apparatus as claimed in claim 1, wherein the catalyst is a carbon filter.

5. An apparatus as claimed in claim 1, wherein the outlet comprises a nozzle or nozzles for directing the stream of air from which steriliant has been removed into the atmosphere around the enclosure to create turbulence in the air.

6. An apparatus as claimed in claim 3, wherein the means for circulating air containing steriliant through the part of the enclosure downstream of the catalyst during the room sterilization process comprises at least one fan having a throughput lower than the throughput of the means for drawing steriliant containing air and having a further inlet disposed in the enclosure on the downstream side of the catalyst to draw air containing steriliant from the atmosphere into the enclosure during the room sterilization process and to circulate air through the downstream side of the enclosure to sterilize that part of the enclosure, the air containing steriliant being released from the enclosure by the outlet from the enclosure.

7. An apparatus as claimed in claim 1, wherein the apparatus is mounted on wheels to be readily mobile.

* * * * *

UNITED STATES PATENT AND TRADEMARK OFFICE
CERTIFICATE OF CORRECTION

PATENT NO. : 7,132,083 B2  
APPLICATION NO. : 10/276193  
DATED : November 7, 2006  
INVENTOR(S) : Martin Page 1 of 1

It is certified that error appears in the above-identified patent and that said Letters Patent is hereby corrected as shown below:

Column 2
Line 11, change "$H_2O_2$" to --$H_2O$--

Column 3
Line 11, after "mounted on" remove |,|
Line 31, after "fan" insert --14--

Signed and Sealed this

Seventeenth Day of June, 2008

JON W. DUDAS
*Director of the United States Patent and Trademark Office*

UNITED STATES PATENT AND TRADEMARK OFFICE
CERTIFICATE OF CORRECTION

PATENT NO. : 7,132,083 B2
APPLICATION NO. : 10/276193
DATED : November 7, 2006
INVENTOR(S) : Martin It is certified that error appears in the above-identified patent and that said Letters Patent is hereby corrected as shown below:

Column 2

Line 57, remove [to]

Signed and Sealed this

Twentieth Day of July, 2010

David J. Kappos
*Director of the United States Patent and Trademark Office*